United States Patent [19]
Abadi et al.

[11] Patent Number: 5,199,453
[45] Date of Patent: Apr. 6, 1993

[54] METHOD FOR CONTROL OF HARD WATER SCALE DEPOSITION IN EVAPORATIVE COOLING SYSTEMS

[75] Inventors: Khodabandeh Abadi, P.O. Box 2425, Tucson, Ariz. 85702; Craig A. Hunt, Tucson, Ariz.

[73] Assignee: Khodabandeh Abadi, Tucson, Ariz.

[21] Appl. No.: 790,006

[22] Filed: Dec. 5, 1991

Related U.S. Application Data

[62] Division of Ser. No. 614,856, Nov. 16, 1990, Pat. No. 5,101,851, which is a division of Ser. No. 495,351, Mar. 19, 1990, Pat. No. 5,013,488.

[51] Int. Cl.$^5$ ............................................. G05D 11/13
[52] U.S. Cl. ............................................. 137/3; 137/91
[58] Field of Search ................................. 137/3, 4, 91

[56] References Cited

U.S. PATENT DOCUMENTS

| | | |
|---|---|---|
| 2,543,522 | 2/1951 | Cohen. |
| 2,869,831 | 1/1959 | Brockelsby ............... 137/91 X |
| 3,195,551 | 7/1965 | Russell ..................... 137/91 X |
| 3,282,277 | 11/1966 | Hayman ..................... 137/3 |
| 3,485,257 | 12/1969 | Gegenheimer et al. ........ 137/91 |
| 3,557,817 | 1/1971 | Royse ....................... 137/91 |
| 3,754,741 | 8/1973 | Whitehurst ................. 137/3 X |
| 4,982,755 | 1/1991 | Roberts et al. ............. 137/91 X |

FOREIGN PATENT DOCUMENTS 741512  8/1966  Canada ................................ 137/3

*Primary Examiner*—Stephen M. Hepperle
*Attorney, Agent, or Firm*—Thomas H. Whaley

[57] ABSTRACT

Disclosed is a method and apparatus for preventing or minimizing scale deposition from hard water onto heat transfer surfaces in atmospheric cooling towers, such as those used in air conditioning and refrigeration systems, where evaporative cooling of water provides the necessary heat sink to the atmosphere. An electrical/mechanical control system responsive to changes in density of the water in the evaporative cooling system operates to permit discharge of water containing dissolved and suspended solids from the system when its density reaches a predetermined maximum value and to discontinue the discharge of cooling system water when its density reaches a predetermined minimum value. Water drained from the cooling system is replaced by fresh water, preferably by water containing chemical additives to increase solubility of hard water minerals in the cooling water.

4 Claims, 3 Drawing Sheets

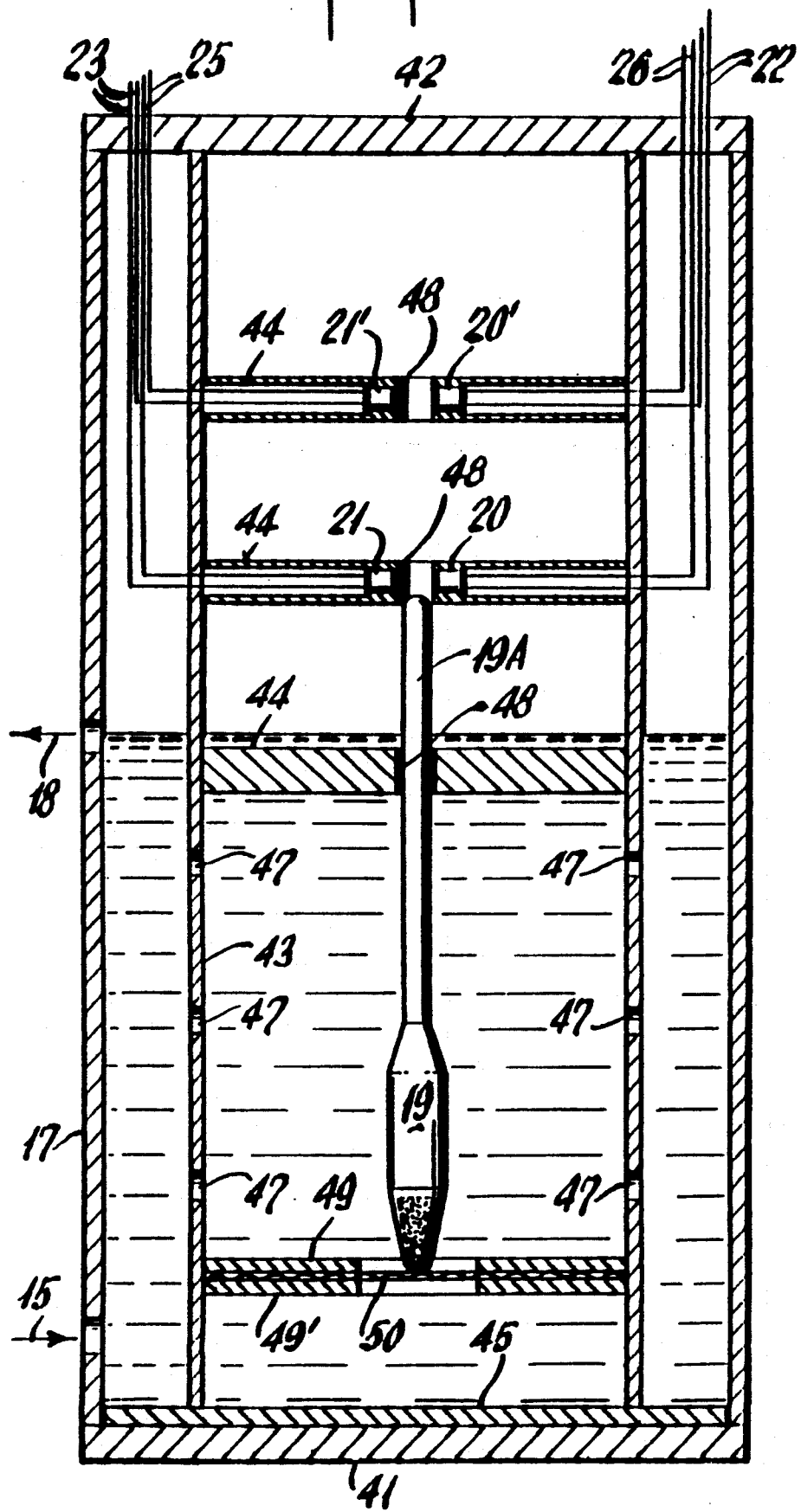

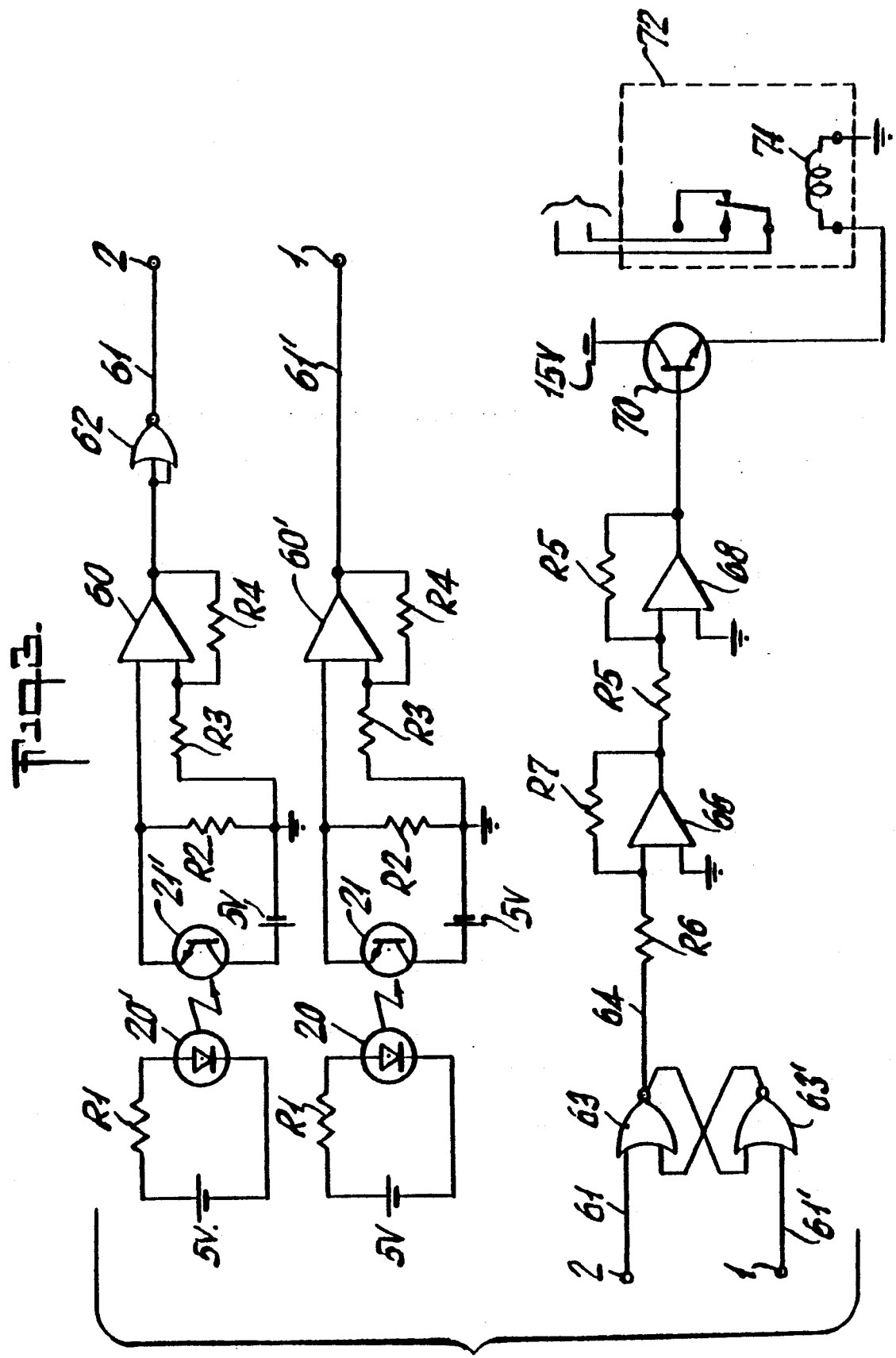

METHOD FOR CONTROL OF HARD WATER SCALE DEPOSITION IN EVAPORATIVE COOLING SYSTEMS

This application is a divisional application of my copending U.S. patent application Ser. No. 614,856, filed Nov. 16, 1990 now U.S. Pat. No. 5,101,851, as a divisional application of Ser. No. 495,351, filed Mar. 19, 1990, now U.S. Pat. No. 5,013,488, issued May 7, 1991.

BACKGROUND OF THE INVENTION

This invention relates to a method and means for preventing or minimizing the deposition of scale from hard water on water wet surfaces in evaporative cooling systems.

In the operation of an evaporative cooling system, water is lost from the system by evaporation which helps to cool the remaining water. As water is lost by evaporation, make-up water is added to maintain the required water inventory in the system. At the same time, however, dissolved minerals are left behind by the evaporating water so that as more and more water is lost by evaporation, the concentration of dissolved solids in the remaining water grows greater and greater. Eventually, the concentration of dissolved solids reaches and exceeds the saturation level with the result that solids begin to precipitate out of the water solution, and deposit as scale on the heat exchange surfaces associated with the evaporative cooling system. Scaling on heat transfer surfaces decreases the rate of heat transfer. The loss of heat transfer efficiency leads not only to increased operating costs but also to deterioration of equipment.

A common method of preventing the build-up of dissolved minerals in the water of an evaporative cooling system involves the addition of chemicals, e.g. ethylenediaminetetraacetic acid, to maintain the scale forming solids in solution, periodically draining a portion of the water containing dissolved scale and adding fresh make-up water. Many proposals for preventing scale deposition have been made. A leading method involves chemical treatment of the water, measuring the conductivity of the water in the system, draining water containing dissolved solids from the system in response to the conductivity measurement when the preset limit on dissolved solids is reached and supplying fresh water and chemicals to the system. Even will such a method, there is a need for one which does not require as much drainage of water from the system and therefore lower chemicals consumption. As described in greater detail hereafter, this invention provides a reliable method of limiting the build-up of dissolved minerals in the water of an evaporative cooling system to a predetermined level and at the same time restricting the drainage of water. The method is automated by a reliable but comparatively inexpensive means for carrying out the control method.

SUMMARY OF THE INVENTION

In accordance with this invention, the method of control of the build-up of solids in the water of an evaporative cooling system is based on a density measuring device.

The density measurement device of this invention comprises a sampling vessel or chamber connected to the cooling system and arranged for the flow therethrough of some of the water and associated suspended solids circulating through the system, a hydrometer in the chamber, means responsive to the float position, i.e., when the float rises a predetermined distance relative to the surface of the water due to increasing density of the system water, and valve operating means for opening a valve in a water discharge line to discharge water from the system.

A level control valve in the make-up water line admits water and chemicals into the system to replenish that which is discarded as well as that lost by evaporation. When this valve in the make-up water lines opens, the flow of water through a flowmeter associated with the chemical feed device promptly activates an associated pump to inject a predetermined proportion of the chemical solution into fresh water entering cooling system. The relative proportions of chemical solution and water is based on the hardness of the available water supply. The rate of injection of chemicals is based on the flow rate of the make-up water through the flowmeter. A practical device for dispensing chemicals into a stream of water is marketed by Liquid Metronics Inc., an established supplier of water treatment equipment. This operation of discharging water containing a high solids content from the system and adding fresh makeup water and chemical additives continuous until the float in the sampling chamber reaches a predetermined lower position at which time the valve operating means acts to close the valve in the water discharge line. The cycle is repeated as often as necessary during operation of the cooling system.

Many such chemicals and chemical compositions for water treatment are marketed. However, the preferred chemical composition for use in this invention is the composition marketed under the registered trademark Scalesolve by Descale-It Products Company, of Tucson, Ariz., described in U.S. Pat. No. 4,595,517. It has been found that the composition has the capability of emulsifying undissolved scale and holding an appreciable amount of precipitated water minerals in suspension without the accumulation of scale on heat transfer surfaces. With such chemical compositions which have the capability of maintaining scale forming precipitates in suspension, the system water can be permitted to have such a build-up of hardness and suspended minerals that the density of the water can go as high as about 1.04 grams per milliliter (g/ml) without substantial deposition of scale on heat transfer surfaces. In normal operation, it is preferred to maintain the density in the range of 1.004 to 1.02 g/ml.

An economically important feature of the invention is that it is unnecessary to discard large amounts of chemically treated system water in order to avoid scaling in heat exchangers. Many existing cooling systems have a preset rate of continuous drainage which is costly both in the wasteful consumption of water and of the chemical added to it to prevent scale formation.

BRIEF DESCRIPTION OF THE DRAWINGS

For a better understanding of the invention, the further description thereof will refer to the accompanying drawings of which:

FIG. 2 is a detailed cross sectional view of the hydrometer float chamber of FIG. 1 illustrating a preferred method of control of the density of water in an evaporative cooling system.

FIG. 3 is a schematic diagram of electrical and electronic circuitry illustrating a preferred embodiment of apparatus forming part of this invention.

DESCRIPTION OF A PREFERRED EMBODIMENT

Figure 1:
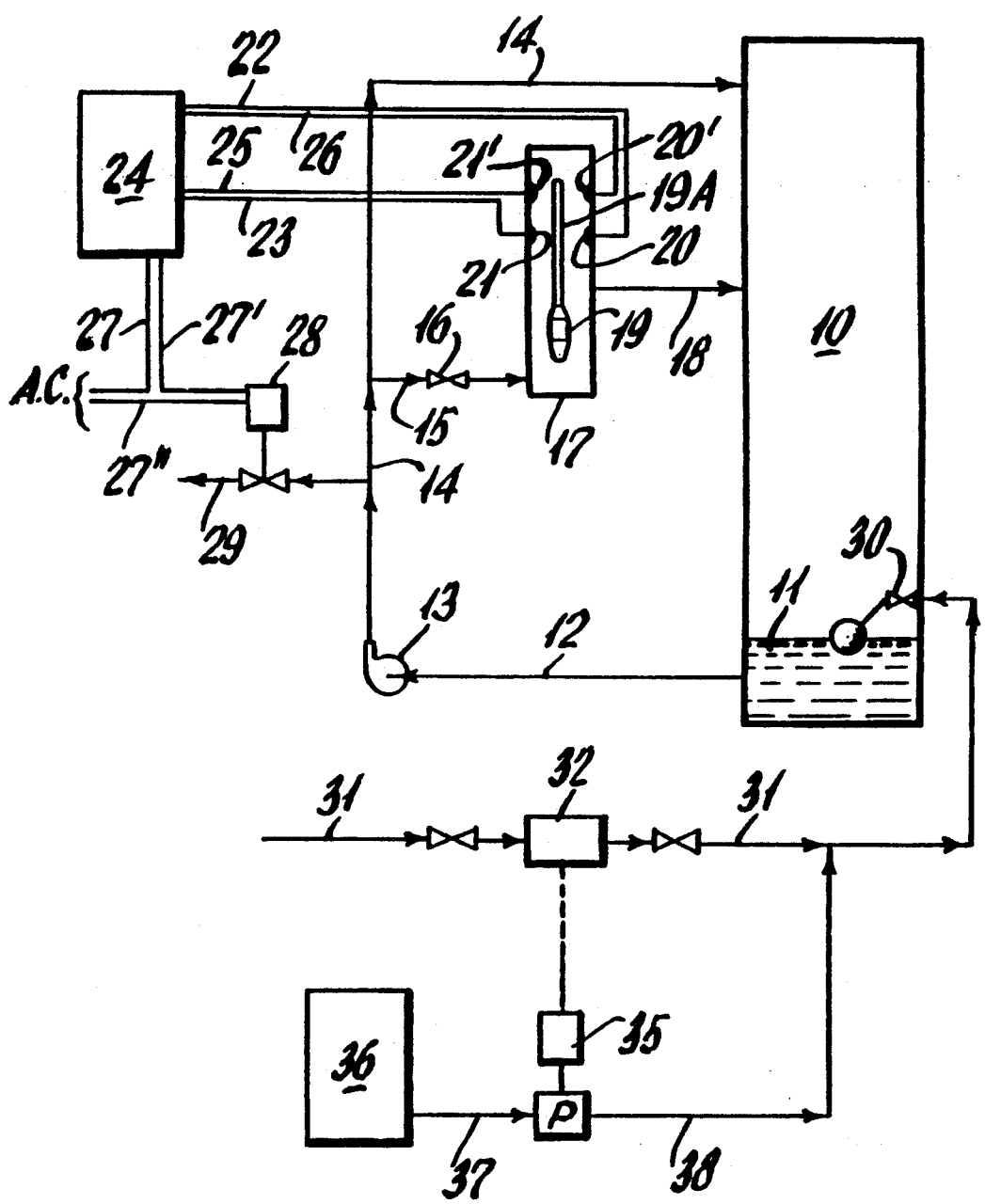
FIG. 1 is a diagrammatic elevational view of an evaporative cooling system illustrating a preferred embodiment of the invention.

With reference to FIG. 1, illustrating one specific preferred embodiment of apparatus suitable for carrying out the method of this invention, reference numeral 10 designates an atmospheric cooling tower of an evaporative cooling system. Inasmuch as the fans, pumps, heat exchangers and piping conventional in such systems are not essential to the description of this invention, they have been omitted in the interest of clarity. Sump 11 of tower 10 is connected by pipe 12 to pump 13 which continuously recirculates water from the sump 11 via pipe 14 to the top of tower 10. A sample line 15 provided with needle valve 16 serves to pass a slip stream of water from pipe 14 to sampling chamber 17 which has overflow pipe 18 draining into tower 10. A hydrometer 19 floats in the pool of water in the lower part of chamber 17. Light emitting diodes 20 and 20' opposite a pair of detectors 21 and 21' are positioned in the upper portion of chamber 17. When the water passing through chamber 17 has a density equal to or exceeding a predetermined value, e.g., 1.02 g/ml, hydrometer 19 rises in the water pool and the tip of its spindle 19A will interrupt the light beam directed from light source 20 to light detector 21 both of which are connected by wires 22 and 23, respectively, to circuit board 24. Similarly, light source 20' and light detector 21' are connected to circuit board 24 as described in more detail hereinafter by wires 25 and 26.

When spindle 19A of hydrometer 19 rises and intersects the light beam of emitter 20' preventing it from impinging on detector 21' because the water in chamber 17 has a density equal to or exceeding the selected maximum, the circuitry of board 24 sends electrical power via wires 27, 27' and 27" to normally closed solenoid valve 28 in drain line 29 causing valve 28 to open and thus discard water from the cooling system.

As water is discarded from the system through pipe 29, the liquid level in sump 11 of tower 10 falls and causes float-controlled valve 30 to open so that fresh make-up water containing chemical additives from supply pipe 31 flows into sump 11. Flowmeter-pulser 32, responsive to the rate of flow of makeup water through pipe 31 sends electrical pulses to a diaphragm type liquid metering pump 35 which delivers precise amounts of chemical additive from chemical supply tank 36 through pipe 37 to pump 35 and from pump 35 through pipe 38 to make up water supply line 31.

Hence, when valve 30 opens and make-up water flows through pipe 31 an electrical signal from flowmeter-pulser 32 is transmitted to and activates pump 35 so that chemical from tank 36 is injected via line 38 into the make-up water flowing through pipe 31. The proportion of chemical to make-up water is preset and controlled by flowmeter-pulser 32. As previously mentioned, the selected proportioning is based on the hardness of fresh make-up water and the effectiveness of the injected chemical or chemical composition.

During the simultaneous discharge of system water from pipe 29 and introduction of fresh water through pipe 31, the density of the system water continuously recirculated through pipes 12, 14, 15, 18 gradually decreases and ultimately drops to or below a preselected value. As hydrometer 19 moves downward in chamber 17 responsive to the decrease in density of the water in the system, it reaches a point where spindle 19A no longer obstructs the light beam from source 20 to detector 21. When detector 21 detects light from light source 20 it sends a signal to the circuitry of circuit board 24, which in turn acts to cause solenoid valve 28 to close. When the discharge of system water is stopped, the flow of make-up water to sump 11 soon raises the water level therein sufficiently to cause level control valve 30 to close stopping the flow of water through flowmeter-pulser 32 and the flow of chemical additive through lines 37 and 38.

With valve 28 closed, the flowmeter-pulser 32 and chemical feed device 35 are in stand-by condition ready to become operative when the float valve 30 calls for make-up water addition due to evaporation of water in the system. When the density of the system water passing through sampling chamber 17 causes spindle 19A to interrupt the light beam directed by source 20 toward detector 21, solenoid valve 28 is opened to discharge system water and the consequent drop of water level in sump 11 opens level control valve 30 to replenish the water discarded from the system, thus completing the cycle.

Sampling chamber 17 is shown diagrammatically in FIG. 1 in its basic form. FIG. 2 shows details of chamber 17 with additional elements that maintain hydrometer 19 in a central position and that minimize water current impingement on hydrometer 19.

With references to FIG. 2, vessel 17 is desirably a clear plastic tube capped at its opposite ends by plastic disks 41 and 42. Another clear plastic tube 43 of smaller diameter than vessel 17 is held concentrically within tube 17 by disk 45. The lower portion of inner tube 43 has several small openings or perforations 47 which permit water entering outer tube 17 through pipe 15 to pass into and out of tube 43 on its way to drain pipe 18. Tube 43 with perforations 47 serves to minimize the impingement on hydrometer 19 of the water-current flowing through chamber 17. The upper portion of inner tube 43 contains several vertically spaced horizontal plastic disks 44 each with a central opening 48 of slightly larger diameter than the diameter of spindle 19A of hydrometer 19. Thus, disks 44 act to keep spindle 19A substantially aligned with the axis of chamber 17 and tube 43. The central openings 48 are only large enough to allow spindle 19A to move freely up and down as the density of the water passing through chamber 17 varies. The top portion of inner tube 43 is provided with light sources 20 and 20' and light detectors 21 and 21' mounted therein in diametrically opposite positions. Wiring 22, 23, 24, 25, associated with light sources 20 and 20' and light detectors 21 and 21' is illustrated as exiting vessel 17 through top disk 42 but may, if desired, pass through the wall of tube 17.

The inner tube 43 is also provided near its lower end with a pair of disks 49 and 49', each having an opening at its center larger than the tip of hydrometer 19. A screen 50 sandwiched between plates 49 and 49' extends over the central opening and is held in place by the plates. The screen 50 limits the downward travel of hydrometer 19 in the event that the water level in sampling chamber 17 falls below the level of outlet line 18.

A preferred specific embodiment of an electrical circuit capable of performing the above described functions is illustrated in FIG. 3. With reference to this figure, infrared light emitting diodes 20 and 20' are paired with infrared detectors 21 and 21' in conventional circuits wherein 5 V is a 5 volt power source and resistors $R_1$ limit the current passing through the infrared light emitting diodes. When infrared light is received by the infrared detector 21 or 21' its resistance decreases allowing a large increase in current to flow from its 5 volt power source 5 V through the detector, which, in turn, causes a large increase in voltage drop across its resistor $R_2$. For example, in this particular circuit, when $R_2$ has a value of 1000 ohms the voltage drop varies from nearly 0 when the beam is blocked by stem 19' of the hydrometer 19 to about 3.5 volts when the infrared beam is not blocked.

The voltage drop across resistor $R_2$ supplies the desired operational control signal for operation of the control system via operational amplifiers 60 and 60' which operate as non-inverting amplifiers. The gain in voltage $R_4/R_3$, increases the voltage in line 61 by an amount sufficient, e.g. 12 to 15 volts, to ensure an "on" position at the NOR gates as described hereinafter. A NOR gate 62 in line 62 inverts the polarity of the signal in line 61. The two signals in lines 61 and 61' are transmitted to NOR gates 63 and 63' arranged as shown in the drawings to function as an RS flip-flop, a simple logic circuit of conventional design well known in the art.

In the particular circuit illustrated, the output from the flip-flop circuit 63, 63' passes through line 64 and through two operational amplifiers 66 and 68 which operate as inverting amplifiers in series to an NPN, 10–50 hFE power transistor 70. Power transistor 70 acts as a switch to permit current to flow from a 15 volt power source 15 V through the solenoid winding 71 of a double pole, double throw relay switch 72 of conventional design which activates solenoid valve 28 of FIG. 1. The +12 volt supply to the base lead of transistor 70 produces approximately 11.4 volts at 90 milliamperes at the emitter lead to energize the solenoid winding 71 of relay switch 72 which, in turn, allows current to flow through lines 27, 27' and 27" energizing the solenoid of valve 28 opening the valve. When no signal is supplied to the transistor 70 from amplifier 68, no current flows from voltage source 15 V which then allows valve 28 of FIG. 1 to return to its normally closed position.

In the specific embodiment of the control circuit illustrated in FIG. 3, the following values of resistors $R_1$ through $R_8$ are listed in Table I.

TABLE I

| Resistor | Value |
| --- | --- |
| $R_1$ | 430 ohms |
| $R_2$ | 1000 ohms |
| $R_3$ | 1.5 megohms |
| $R_4$ | 6.8 megohms |
| $R_5$ | 1.6 megohms |
| $R_6$ | 2.0 megohms |
| $R_7$ | 1.6 megohms |
| $R_8$ | 1000 ohms |

We claim:

1. A method of control of the buildup of mineral solids in hard water in an evaporative cooling system which comprises:
 a) detecting changes in density of water in the system containing dissolved and suspended hard water solids,
 b) discharging water containing dissolved and suspended solids from the system when the density of the water in the system reaches a predetermined maximum value in the range of from about 1.02 to 1.04 grams per milliliter,
 c) adding make up water to the system to replace the water discharged from the system,
 d) continuing steps b) and c) until the density of the water in the system reaches a predetermined minimum value in the range of from about 1.004 to about 1.01 measured at ambient water temperature,
 e) discontinuing steps b) and c) until the density of the water in the system again reaches the predetermined maximum value, and
 f) repeating steps a) through e).

2. A method according to claim 1 wherein the water evaporated from the system is replaced with makeup water as needed in the interval between steps d) and b).

3. A method according to claim 2 wherein the makeup water is added as required to maintain a substantially constant amount of water in the system.

4. A method according to claim 1 wherein step a) is performed on an aliquot sample of water in the system.

* * * * *